(12) United States Patent
SenGupta et al.

(10) Patent No.: US 7,888,306 B2
(45) Date of Patent: *Feb. 15, 2011

(54) COMPOSITIONS CONTAINING BENEFIT AGENT COMPOSITES PRE-EMULSIFIED USING COLLOIDAL CATIONIC PARTICLES

(75) Inventors: Ashoke K. SenGupta, Barrington, IL (US); Ilona Lin, Wauconda, IL (US); Jason St. Onge, Geneva, IL (US); Melanie J. Hughes, Chester (GB)

(73) Assignee: Amcol International Corporation, Hoffman Estates, IL (US)

( * ) Notice: Subject to any disclaimer, the term of this patent is extended or adjusted under 35 U.S.C. 154(b) by 360 days.

This patent is subject to a terminal disclaimer.

(21) Appl. No.: 12/152,364

(22) Filed: May 14, 2008

(65) Prior Publication Data

US 2008/0286367 A1 Nov. 20, 2008

Related U.S. Application Data

(60) Provisional application No. 60/917,832, filed on May 14, 2007.

(51) Int. Cl.
C11D 3/37 (2006.01)
C11D 1/86 (2006.01)

(52) U.S. Cl. .................. 510/417; 510/119; 510/130; 510/155; 510/235; 510/251; 510/326; 510/334; 510/353; 510/422; 510/437

(58) Field of Classification Search .................. 510/417, 510/119, 130, 155, 235, 251, 326, 334, 353, 510/422, 437
See application file for complete search history.

(56) References Cited

U.S. PATENT DOCUMENTS

| | | | |
|---|---|---|---|
| 2,800,457 A | 7/1957 | Green et al. | |
| 3,041,288 A | 6/1962 | Anthony | |
| 3,415,758 A | 12/1968 | Powell et al. | |
| 3,516,941 A | 6/1970 | Matson | |
| 3,723,325 A | 3/1973 | Parran, Jr. | |
| 3,870,542 A | 3/1975 | Ida et al. | |
| 4,145,184 A | 3/1979 | Brain et al. | |
| 4,152,272 A | 5/1979 | Young | |
| 4,318,818 A | 3/1982 | Letton et al. | |
| 4,387,090 A | 6/1983 | Bolich, Jr. | |
| 4,402,856 A | 9/1983 | Schnoring et al. | |
| 4,424,134 A | 1/1984 | Sissin et al. | |
| 4,446,032 A | 5/1984 | Munteanu et al. | |
| 4,446,042 A | 5/1984 | Leslie | |
| 4,464,271 A | 8/1984 | Munteanu et al. | |
| 4,515,705 A | 5/1985 | Moeddel | |
| 4,524,787 A * | 6/1985 | Khalil et al. ............ 132/204 |
| 4,534,891 A | 8/1985 | Boden et al. | |
| 4,537,706 A | 8/1985 | Severson, Jr. | |
| 4,537,707 A | 8/1985 | Severson, Jr. | |
| 4,550,862 A | 11/1985 | Barker et al. | |
| 4,561,998 A | 12/1985 | Wertz et al. | |
| 4,597,898 A | 7/1986 | Vander Meer | |
| 4,664,064 A | 5/1987 | Lowe | |
| 4,673,568 A | 6/1987 | Grollier et al. | |
| 4,690,825 A | 9/1987 | Won | |
| 4,705,681 A | 11/1987 | Maes et al. | |
| 4,710,374 A | 12/1987 | Grollier et al. | |
| 4,714,562 A | 12/1987 | Roselle et al. | |
| 4,767,547 A | 8/1988 | Straathof et al. | |
| 4,842,849 A | 6/1989 | Grollier et al. | |
| 4,946,624 A | 8/1990 | Michael | |
| 4,948,818 A | 8/1990 | Carmody et al. | |
| 4,954,285 A | 9/1990 | Wierenga et al. | |
| 4,962,133 A | 10/1990 | Chromecek et al. | |
| 4,962,170 A | 10/1990 | Chromecek et al. | |
| RE33,429 E | 11/1990 | Abrutyn | |
| 4,968,451 A | 11/1990 | Scheibel et al. | |
| 4,973,422 A | 11/1990 | Schmidt | |
| 5,015,469 A * | 5/1991 | Yoneyama et al. ............ 424/59 |
| 5,085,857 A | 2/1992 | Reid et al. | |
| 5,112,688 A | 5/1992 | Michael | |
| 5,126,061 A | 6/1992 | Michael | |
| 5,137,646 A | 8/1992 | Schmidt et al. | |
| 5,145,842 A | 9/1992 | Driedger et al. | |
| 5,169,552 A | 12/1992 | Wise | |

(Continued)

FOREIGN PATENT DOCUMENTS

WO  WO 98/11869  3/1998

(Continued)

*Primary Examiner*—Charles I Boyer
(74) *Attorney, Agent, or Firm*—Marshall, Gerstein & Borun LLP

(57) ABSTRACT

A cleansing or a surface-conditioning composition comprising a mixture of (i) and (ii) in water: i) a surfactant selected from the group consisting of anionic, non-ionic, zwitterionic, cationic, and mixtures thereof; and ii) a hydrophobic benefit agent in a particulate form having a mean particle size in the range of 1-1,000 micron, and a specific gravity of $\geq 1$, not encapsulated within a film or a capsule-like enclosure, the particulate hydrophobic benefit agent comprising: a) a physically-modified form of the hydrophobic benefit agent; and b) a deposition-aid material bonded to the surface of the physically-modified benefit agent material, wherein the bonding between the two said materials is achieved prior to addition to i), wherein said deposition-aid material is not a surfactant having a weight average molecular weight of less than 5,000 Dalton.

22 Claims, No Drawings

U.S. PATENT DOCUMENTS

| | | | |
|---|---|---|---|
| 5,194,639 A | 3/1993 | Connor et al. | |
| 5,207,998 A | 5/1993 | Robinson et al. | |
| 5,275,755 A | 1/1994 | Sebag et al. | |
| 5,288,417 A | 2/1994 | Bauer et al. | |
| 5,288,431 A | 2/1994 | Huber et al. | |
| 5,306,434 A | 4/1994 | Schueller et al. | |
| 5,403,499 A | 4/1995 | Kiefer et al. | |
| 5,411,671 A | 5/1995 | Bauer et al. | |
| 5,443,760 A * | 8/1995 | Kasprzak | 424/78.03 |
| 5,458,809 A | 10/1995 | Fredj et al. | |
| 5,458,810 A | 10/1995 | Fredj et al. | |
| 5,460,752 A | 10/1995 | Fredj et al. | |
| 5,466,802 A | 11/1995 | Panandiker et al. | |
| 5,470,507 A | 11/1995 | Fredj et al. | |
| 5,500,152 A | 3/1996 | Helliwell | |
| 5,543,074 A | 8/1996 | Hague et al. | |
| 5,545,340 A | 8/1996 | Wahl et al. | |
| 5,545,350 A | 8/1996 | Baker et al. | |
| 5,559,261 A | 9/1996 | Sivik | |
| 5,562,849 A | 10/1996 | Wahl et al. | |
| 5,565,145 A | 10/1996 | Watson et al. | |
| 5,574,179 A | 11/1996 | Wahl et al. | |
| 5,581,005 A | 12/1996 | Perkins | |
| 5,597,936 A | 1/1997 | Perkins et al. | |
| 5,618,523 A | 4/1997 | Zysman et al. | |
| 5,661,118 A | 8/1997 | Cauwet et al. | |
| 5,674,832 A | 10/1997 | Keys | |
| 5,677,407 A | 10/1997 | Sojka | |
| 5,679,630 A | 10/1997 | Baeck et al. | |
| 5,703,030 A | 12/1997 | Perkins et al. | |
| 5,703,034 A | 12/1997 | Offshack et al. | |
| 5,705,464 A | 1/1998 | Scheper et al. | |
| 5,712,358 A | 1/1998 | Sojka | |
| 5,726,138 A * | 3/1998 | Tsaur et al. | 510/158 |
| 5,731,278 A | 3/1998 | Nair et al. | |
| 5,756,436 A | 5/1998 | Royce et al. | |
| 5,759,990 A | 6/1998 | Wahl et al. | |
| 5,776,443 A | 7/1998 | Vinski et al. | |
| 5,777,054 A | 7/1998 | Sojka | |
| 5,817,298 A * | 10/1998 | Galley et al. | 424/59 |
| 5,830,960 A | 11/1998 | Sojka | |
| 5,830,967 A | 11/1998 | Sojka | |
| 5,834,577 A | 11/1998 | Sojka | |
| 5,837,661 A | 11/1998 | Evans et al. | |
| 5,837,790 A | 11/1998 | Sojka | |
| 5,853,707 A | 12/1998 | Wells et al. | |
| 5,853,711 A * | 12/1998 | Nakamura et al. | 424/78.03 |
| 5,877,145 A | 3/1999 | Wahl et al. | |
| 5,902,781 A | 5/1999 | Painter | |
| 5,914,101 A | 6/1999 | Tapley et al. | |
| 5,914,307 A | 6/1999 | DeNome et al. | |
| 5,916,862 A | 6/1999 | Morelli et al. | |
| 5,923,203 A | 7/1999 | Chen et al. | |
| 5,929,022 A | 7/1999 | Velazquez | |
| 5,932,203 A | 8/1999 | Coffindaffer et al. | |
| 5,935,561 A | 8/1999 | Inman et al. | |
| 5,939,373 A | 8/1999 | Haeggberg et al. | |
| 5,955,552 A | 9/1999 | Sojka | |
| 5,962,386 A | 10/1999 | Scheper et al. | |
| 5,968,286 A | 10/1999 | Crudele et al. | |
| 5,968,881 A | 10/1999 | Haeggberg et al. | |
| 5,990,059 A | 11/1999 | Finel et al. | |
| 5,990,065 A | 11/1999 | Vinson et al. | |
| 6,017,871 A | 1/2000 | Baeck et al. | |
| 6,020,294 A | 2/2000 | Getty et al. | |
| 6,024,943 A | 2/2000 | Ness et al. | |
| 6,051,540 A | 4/2000 | Shefer et al. | |
| 6,069,122 A | 5/2000 | Vinson et al. | |
| 6,080,708 A | 6/2000 | Glenn, Jr. et al. | |
| 6,107,429 A | 8/2000 | Sojka | |
| 6,126,954 A | 10/2000 | Tsaur | |
| 6,156,713 A | 12/2000 | Chopra et al. | |
| 6,162,423 A | 12/2000 | Sebag et al. | |
| 6,248,849 B1 | 6/2001 | Sojka | |
| 6,261,483 B1 | 7/2001 | Frank et al. | |
| 6,277,361 B1 | 8/2001 | Murray | |
| 6,323,246 B1 * | 11/2001 | Nakama et al. | 516/27 |
| 6,329,057 B1 | 12/2001 | Dungworth et al. | |
| 6,335,315 B1 | 1/2002 | Trinh et al. | |
| 6,387,995 B1 | 5/2002 | Sojka | |
| 6,436,383 B2 | 8/2002 | Murray | |
| 6,503,495 B1 * | 1/2003 | Alwattari et al. | 424/70.7 |
| 6,528,070 B1 * | 3/2003 | Bratescu et al. | 424/401 |
| 6,541,565 B2 | 4/2003 | Hood et al. | |
| 6,667,029 B2 | 12/2003 | Zhong et al. | |
| 6,706,258 B1 | 3/2004 | Gallagher et al. | |
| 6,740,631 B2 | 5/2004 | Shefer et al. | |
| 6,790,814 B1 | 9/2004 | Marin et al. | |
| 6,844,302 B1 | 1/2005 | Boden et al. | |
| 6,936,264 B2 * | 8/2005 | Glenn et al. | 424/401 |
| 6,972,129 B1 * | 12/2005 | Ogawa et al. | 424/401 |
| 7,118,057 B2 | 10/2006 | Hao | |
| 7,119,057 B2 | 10/2006 | Popplewell et al. | |
| 7,119,060 B2 | 10/2006 | Shefer et al. | |
| 7,122,512 B2 | 10/2006 | Brain et al. | |
| 7,125,835 B2 | 10/2006 | Bennett et al. | |
| 7,196,049 B2 | 3/2007 | Brain et al. | |
| 7,294,612 B2 | 11/2007 | Popplewell et al. | |
| 2003/0049282 A1 * | 3/2003 | Aronson et al. | 424/401 |
| 2003/0224954 A1 | 12/2003 | Wells et al. | |
| 2003/0228339 A1 | 12/2003 | El-Nokaly et al. | |
| 2005/0158266 A1 | 7/2005 | Peffly et al. | |
| 2005/0227907 A1 | 10/2005 | Lee et al. | |
| 2005/0244356 A1 | 11/2005 | Aronson et al. | |
| 2006/0014655 A1 | 1/2006 | Smets et al. | |
| 2007/0166262 A1 * | 7/2007 | Pratley et al. | 424/70.12 |

FOREIGN PATENT DOCUMENTS

| | | |
|---|---|---|
| WO | WO 98/11870 | 3/1998 |
| WO | WO 01/74310 | 10/2001 |

* cited by examiner

COMPOSITIONS CONTAINING BENEFIT AGENT COMPOSITES PRE-EMULSIFIED USING COLLOIDAL CATIONIC PARTICLES

CROSS-REFERENCE TO RELATED APPLICATION

The present application claims the benefit of priority of Provisional Patent Application No. 60/917,832 filed on May 14, 2007. The entire text of the priority application is incorporated herein by reference in its entirety.

FIELD OF THE INVENTION

The present invention relates to compositions that allow increased deposition and retention of benefit agents contained therein, onto a substrate, for example, a fabric; hair; skin; teeth, and other hard surfaces, while the substrate is being treated with these compositions. Cleansing products such as the conditioning shampoos, bodywashes, soaps, detergents, toothpaste, and counter or floor-cleaning products, as well as surface-conditioning products such as fabric softeners are some of the exemplary product forms that these compositions represent. Silicone, fragrance, emollient, ultraviolet (UV) ray absorbers, and antimicrobial agents are typical examples of the benefit agents.

Despite the large number of prior art methods and compositions for enhancing the deposition of benefit agents (e.g., silicone, fragrance) from cleansing products, there is a need for substantially improving the deposition efficiency. The trends in consumer preference related to these products, for example, conditioning shampoos and moisturizing bodywashes, illustrate this void. Most commercial conditioning shampoos (2-in-1 shampoos) contain a water-immiscible silicone fluid as a hair conditioning agent, with the silicone fluid remaining dispersed in the form of oil-in-water (O/W) emulsions in the shampoo base (a water-based solution). The shampoo base further contains a water-soluble, high molecular weight, cationic polymer as a deposition-aid for silicone-deposition on the hair. Yet, most consumers seeking relatively high levels of hair-conditioning prefer conditioners, the products that do not rely on silicone-deposition for hair-conditioning, to the 2-in-1 shampoos. Likewise, most commercial, moisturizing body-wash products contain relatively high amounts of skin-moisturizing emollients such as petrolatum, mineral oil, and vegetable oils, along with a cationic polymer as a deposition-aid. Despite this, consumers tend to rely on moisturizing lotions for skin-moisturizing, likely because of inadequate emollient-deposition on the skin from body-wash products.

Unexpectedly, we have now found that the compositions disclosed herein show an extraordinarily high level of performance properties, namely, hair-conditioning, fabric softening, and skin-moisturizing, which is attributed to the specific additive-form in which the benefit agents are incorporated into these compositions, and in particular to the composition of this additive-form, hitherto not disclosed in the prior art. According to the present invention, the benefit agent is added to the claimed compositions, only after it is decidedly bonded to a deposition-aid, utilizing physical interaction-mediated bonding (i.e., not a chemical bond) between the two materials. Also, prior to being bonded to a deposition-aid, the benefit agent preferably undergoes a physical change, to serve multiple purposes critical to the object of the present invention.

In order to meet the object of the present invention, the aforementioned physical modification of the benefit agent does not involve encapsulation of the benefit agent within a polymeric capsule-like enclosure, an approach revealed in the prior art. Rather, in one embodiment, it involves producing a composite material comprising a water-immiscible, hydrophobic liquid for a benefit agent, and an exfoliated, organophilic smectite clay capable of thickening (increasing the viscosity of) the hydrophobic liquid. In another embodiment, it is a composite material comprising a hydrophobic liquid and an exfoliated, organophilic smectite clay, with the composite material further containing a benefit agent dispersed homogeneously throughout the entire mass of the composite material. The resulting benefit agent composite is necessarily a highly viscous material, having a sufficiently high viscosity for strongly opposing the "roll-up" mechanism, known in the art as being the mechanism by which surfactants remove "oily-soils" from a surface undergoing cleansing by surfactants. Yet another beneficial outcome of the foregoing modification of the benefit agent is that the Hamaker constant, a direct proportionality factor for a measure of the van der Waals attraction between material bodies, of the composite material is significantly higher than that of the benefit agent taken individually. A further benefit is that the specific gravity of the benefit agent composite can be varied starting at a minimum value of about 1, which might be critical to achieving good stability against settling/creaming (by virtue of density-matching between dispersed and continuous phases) of the benefit agent composite when dispersed in the claimed compositions whose solution phase could have a specific gravity of 1 or higher.

The deposition-aid material is not a surfactant but most preferably a cationic, colloidal (<2 micron in size), particulate material having a relatively high surface charge. In being physically bonded to (adsorbed on) the benefit agent composite, the cationic deposition-aid particles remain adsorbed on the surface of the composite, but without forming any continuous film or capsule-wall around the composite. These cationic particles can comprise cationic polymers including the cationic deposition polymers known in the art. The relatively high surface charge of the deposition-aid particles bound to the benefit agent-containing composite, contributes towards the dispersion-stability (i.e., against flocculation and coalescence) of the composite material, when the material is dispersed in aqueous solutions including surfactant solutions.

In producing the foregoing additive-form for the benefit agent, a water-immiscible, composite material composition comprising a hydrophobic liquid (which itself can be a benefit agent), an exfoliated smectite clay, and a benefit agent, is dispersed in water using a dispersing agent (an emulsifier system) comprising colloidal, water-insoluble, cationic particles having a relatively high cationic surface charge. The surface properties, including hydrophobicity and surface charge (as defined and characterized by methods known in the art), of these cationic particles and the benefit agent composite are such that the cationic particles can remain adsorbed on the surface of the benefit agent composite. The organophilic (i.e., hydrophobic) smectite clay component of the benefit agent composite is such that a portion of the clay surface bears an anionic charge, and the hydrophobic modification of the clay surface is at a level wherein exfoliated clay platelets can remain adsorbed at an oil-water interface. The said additive-form of the benefit agent produces a stable, cationic oil-in-water (O/W) emulsion when mixed with or diluted in water, with the benefit agent contained in the oil phase (comprising the above-defined composite material) of the emulsion. The mean particle size of the emulsion droplets is in the range of 1 to about 300 microns, preferably about 5 µm to about 150

μm. The resulting O/W emulsion is subsequently mixed into surfactant-laden final compositions of the present invention, as is or in a dried form.

BACKGROUND OF THE INVENTION

By design, detersive surfactants, generally present in excess in products such as shampoos, bodywashes, liquid soaps, laundry detergents, and toothpaste, are meant to remove dirt, oil, grease, and particulate matter from the hair, skin, fabric, and teeth. Nonetheless, it is desirable that one or more functional materials, called herein "benefit agent" or "active", contained in these cleansing products, can be deposited and retained at relatively high levels on the substrates being cleaned, while maintaining detergency and foaming properties of these products. These actives, having benefits related to hair-care or skin-care or fabric-care or dental-care may range from silicones used as hair-conditioning agents, to emollient oils and fragrances used as skin-moisturizing and aesthetic/sensory property-boosting agents. Most of these benefit agents tend to be expensive, and hence can be included in the detersive products only at relatively low to moderate levels. Adequate deposition and retention of these actives, therefore, is critical to realizing their end-use benefits, when they are to be delivered through shampoos, soaps, laundry detergents, and toothpastes.

The prior art includes numerous patents describing methods for improving the deposition of hydrophobic or water-immiscible actives from detersive or wash-off product compositions, many of which involve the following:
  i) the use of O/W emulsions of benefit agents, wherein a water-immiscible liquid (e.g., silicone), used as a benefit agent, is emulsified in water using an emulsifier selected from nonionic, anionic, and cationic surfactants;
  ii) encapsulation of benefit agents within a polymeric capsule or shell, by curing or hardening a polymeric film as a capsule wall over droplets containing a benefit agent, or by encapsulating a benefit agent within a capsule wall comprising a complex coacervate of polymers, e.g., a complex coacervate comprising a polycation and a polyanion.

A majority of these reported inventions, for example, the ones described in U.S. Pat. Nos. 3,723,325, 5,085,857, 5,500, 152, 5,543,074, 5,776,443, 5,853,707, 5,990,059, 5,935,561, 5,923,203, 6,126,954, 6,156,713, 6,277,361 B1, 6,436,383 B2, 6,706,258 B1, U.S. patent application 2005/0158266, and WO 98/11869 rely on cationic polymers as a deposition-aid. Accordingly, these polymers are often referred to as deposition polymers in the art.

Despite the abundance of patents disclosing cationic polymer-aided methods for enhancing the deposition of hydrophobic benefit agents from surfactant-laden compositions, there is a need for substantially improving the deposition efficiency, given, for example, that most consumers who seek relatively high levels of hair-conditioning prefer conditioners, the non-detersive hair-conditioning products, to the detersive products like 2-in-1 shampoos which typically contain cationic polymers as a deposition-aid. A reason for this consumer preference is that, with the 2-in-1 shampoos, a substantial amount of the hair-conditioning agent, silicone, is rinsed away during shampooing, despite the deposition polymers contained therein.

In light of the distinguishing features of the present invention over the prior art, it appears that one plausible cause for the inadequate performance of the cationic deposition polymers as used in the prior art is that these polymers and the benefit agents are added as separate ingredients in producing the final detersive compositions, i.e., the deposition polymer(s) is not pre-adsorbed or pre-disposed to bind onto the benefit agent(s) as these ingredients are incorporated into the final compositions. As described herein, in order for the cationic polymer to function adequately as a deposition-aid, it must first physically attach onto the benefit agent. Given that most cleansing products contain relatively high amounts of anionic surfactants, and in contrast, relatively low levels of benefit agent(s) and a deposition polymer, binding of the deposition polymer onto the benefit agent may not be possible when these ingredients are added separately as ingredients to the detersive compositions, for reasons such as the following:
  i) factors such as high concentration of anionic surfactants, and strong interaction (electrostatic) between an anionic surfactant and a cationic polymer are likely to favor association between the anionic surfactants and the cationic polymer over that between two weakly interacting, low-level ingredients, the cationic polymer and the hydrophobic benefit agent, especially considering that the commonly used cationic deposition polymers (for example, cationic cellulose and cationic guar derivatives) are mostly hydrophilic polymers that tend to have a low affinity for hydrophobic surfaces such as the surfaces of hydrophobic benefit agents;
  ii) since the amount of an anionic surfactant likely to adsorb on the hydrophobic benefit agent would be much smaller than the amount of the surfactant remaining dissolved (i.e., non-adsorbed) in the solution-phase, the cationic deposition polymer is most likely to (associate) form complexes (anionic complexes in anionic surfactant-rich solutions) with the dissolved surfactant molecules rather than with any surfactant molecules pre-adsorbed on the benefit agent;
  iii) being present at a much higher concentration than any cationic polymer-anionic surfactant complex that could possibly form, and having a diffusivity much higher than that of such a complex, the anionic surfactants might adsorb on the hydrophobic benefit agent far more easily than the polymer-surfactant complex, implying that the cationic deposition polymer may not be able to adsorb on the benefit agent to any considerable extent, when these two materials are added separately as ingredients to anionic surfactant-rich cleansing product compositions; and
  iv) the hydrophobic benefit agent may simply dissolve in the surfactant-rich solution.

In fact, it is often theorized in the art that association between the cationic deposition polymer and the hydrophobic benefit agent is achieved only when the cleansing products get heavily diluted during the course of the rinsing process. Clearly, large portions of the added deposition polymer and the benefit agent would be rinsed off before this optimum dilution level is reached.

Albeit, the prior art reveals approaches other than the use of cationic deposition polymers, for example, as disclosed in the U.S. Pat. Nos. 5,726,138, 6,541,565 B2, and 6,667,029 B2, the commercial detersive products continue to rely on these polymers for the deposition of hydrophobic benefit agents. This is likely because the deposition polymer-free approaches are not commercially viable from the standpoint of cost, product stability, and bulk manufacturing.

The prior art also includes methods wherein hydrophobic benefit agents are encapsulated within a capsule wall comprising a polymeric material. The encapsulated benefit agent is subsequently mixed into a cleansing/wash-off product composition comprising one or more surfactants. This final composition may further contain a cationic polymer, with the cationic polymer coating the capsule wall, as disclosed in U.S. Pat. Nos. 7,118,057 B2 and 7,294,612 B2.

The prior art also teaches that a cationic polymer may be an integral part of a capsule wall enclosing a benefit agent, with the capsule wall comprising a complex coacervate of a polycation and a polyanion, as revealed in WO 98/11870. According to a disclosure in WO 98/11870, the cleansing composition may further contain a cationic polymer-based thickening agent which remains dissolved in the aqueous solution phase of the composition. The encapsulated droplets have a particle size distribution such that at least 10% by weight of the droplets comprises relatively large particles having a diameter of at least 100 microns. As noted in WO 98/11870, the efficacy of the claimed compositions relies heavily on parameters such as the relative hardness/softness and the thickness of the complex coacervate capsule wall, as well as the size of the encapsulated droplets of hydrophobic benefit agents, which would be hard to control in a cost-effective manner, especially during bulk manufacturing. Furthermore, while it might be possible to use a thickening agent in certain cleansing products such as shampoo and bodywash, for minimizing gravity-separation of relatively large suspended droplets (particle size>>1 micron) from a product formulation, avoiding product instability in the way of gravity-separation of a key ingredient, might be impossible for liquid detergents which are generally required to have a relatively low viscosity and hence have a relatively low particulate-suspending ability. In addition to these specific concerns regarding the compositions in WO 98/11870, one skilled in the art would be particularly wary about a major limitation that applies, in general, to any encapsulation approach, as discussed below.

In order to adequately realize the end-use benefits, for example, hair-conditioning, fabric-softening, and fragrance-extension, of the hydrophobic benefit agents, while it is essential that there is substantial deposition of the benefit agents on the treated substrate, it is equally important that the benefit agents, once deposited on the substrate, are available in a physical form that is suitable for providing the desired end-use benefit. For example, deposition of a hydrophobic substance such as silicone on the hair or on a fabric causes hydrophobic-modification of the hair or the fabric surface, which in turn leads to effects that manifest as hair-conditioning or fabric-softening benefits. Nonetheless, if the silicone is encapsulated within a polymeric capsule, and should the encapsulated silicone droplet deposit on a substrate, it is the outer surface of the capsule wall and not the strongly hydrophobic surface of the silicone droplet, which would ultimately impart any effect in the way of modification of the substrate-surface. If the capsule wall is derived from hydrophilic, water-soluble polymers, as disclosed in U.S. Pat. Nos. 7,118,057 B2, 7,294,612, and WO 98/11870B2, the outer surface of the capsule wall may not be able to provide for hydrophobic-modification of the hair or the fabric surface, essential to delivering benefits such as hair-conditioning and fabric-softening.

In other words, even after substantial deposition of a benefit agent, it may not be possible to realize the end-use benefits, if the benefit agent is deposited in an encapsulated form comprising a shell of a capsule wall and an inner core of the benefit agent. In that case, at best, one can hope to see only a partial benefit of the benefit agent, relying on diffusion of the benefit agent through the capsule wall and/or leakage of the same due to any breakage of the capsule wall (for which hardness/softness and thickness of the capsule wall would be the efficacy determining factors, as revealed in WO 98/11870). Such subdued or partial availability of the benefit agent, despite its adequate deposition, may provide for a level of end-use benefit (e.g., fragrance emission) that may be sufficient, for example, for post-wash fragrance-extension, but too little for any appreciable hair-conditioning and fabric-softening.

It is therefore an object of the present invention to provide a more efficient method than the methods described in the prior art, for the deposition and retention of hydrophobic or oil-based benefit agents from detersive and/or rinse-off compositions. It is a further object that the compositions and methods described herein, do not involve encapsulation of benefit agents within any capsule wall, are relatively inexpensive, involve manufacturing steps that are easy to implement or control, and do not adversely affect the stability, detergency, and foaming properties of the cleansing product compositions. A related object is to provide stable, low-cost, compositions that allow significantly high deposition and retention of hydrophobic benefit agents onto substrates being treated with the compositions, including the fabric, hair, and skin.

Furthermore, it would be highly convenient to have hydrophobic benefit agents available in a form which can be incorporated easily into a final product composition. In that vein, it would be of much benefit, if such an additive-form for the benefit agent also served towards attaining an enhanced deposition of the benefit agent. Nonetheless, an important issue to be addressed in producing this additive-form is its long-term storage stability. It is therefore a further object of the compositions and methods to provide a highly stable additive-form for hydrophobic benefit agents, which, when incorporated into final product compositions, leads to an increased deposition of the benefit agents.

Several of the patents cited above, for example, U.S. Pat. No. 6,706,258 B1, describe the use of preformed oil-in-water (O/W) emulsions of hydrophobic benefit agents, wherein the oil-phase containing the benefit agent, is emulsified using (anionic, nonionic) surfactant-based emulsifiers. However, in the reported inventions, wherein a cationic polymer-based deposition-aid was used in conjunction with a preformed emulsion of a hydrophobic benefit agent (or with a hydrophobic benefit agent alone), the cationic polymer additive and the preformed emulsion (or a hydrophobic benefit agent alone) were incorporated into the final detersive composition as separately-added ingredients, i.e., no attempt was made therein to pre-adsorb or bind the cationic polymer additive onto the emulsion droplets (or the hydrophobic benefit agent) and subsequently mixing in the polymer-modified emulsion droplets (or the hydrophobic benefit agent) as a whole ingredient in producing the final detersive composition.

In fact, there is no known prior art document wherein a cationic particle and/or a cationic polymer-based additive was used as part of the emulsifier system used to produce a stable O/W emulsion of a hydrophobic benefit agent, that is subsequently incorporated into a surfactant-containing aqueous composition, with the composition exhibiting enhanced deposition of the hydrophobic benefit agent onto an intended site during use, along with good stability, and minimal detrimental effect on detergency and foaming properties, as in accordance with the compositions and methods described herein.

SUMMARY OF THE INVENTION

Described herein are compositions for use as cleansing and surface-conditioning products like shampoos, body-washes, liquid soaps, laundry detergents, fabric softeners, and toothpaste, which allow substantive retention on the hair, skin, fabric, and tooth/gum, of one or more hydrophobic benefit agents contained therein. According to the compositions and methods described herein, the hydrophobic actives are incorporated into the compositions, as cationic oil-in-water (O/W) emulsions. The compositions may further contain surfactants present either in aqueous solutions or in powder/granular forms, polymers, and hydrophilic solvents selected from water, lower alcohols, glycols, and glycerine.

Although low molecular weight (molecular weight<5,000 Dalton) cationic surfactants could be used as an emulsifier, as revealed in the U.S. Pat. No. 5,306,434 involving non-detersive hair conditioner compositions, to produce the cationic surface charge of emulsion droplets, these surfactants are not preferred for the purpose of the compositions and methods described herein. With these low molecular weight emulsifiers, the emulsion stability would be only modest, while the emulsifier dosage requirement would be relatively high. More importantly, these low molecular weight compounds may not be capable of aiding deposition of benefit agents from detersive compositions.

Emulsions stabilized by particulate- and/or polymer-based emulsifiers generally tend to exhibit a relatively high stability against flocculation and coalescence. Considering this inherent advantage with the aforementioned emulsifiers, the present invention embodies the use of these emulsifiers in producing cationic oil-in-water (O/W) emulsions of the hydrophobic benefit agents. Unexpectedly, we have found now that these cationic emulsions greatly enhance the deposition of hydrophobic benefit agents from detersive compositions onto an intended site during use, e.g., hair shaft, skin, fabric.

According to an important embodiment of the compositions and methods described herein, a key component of the emulsifier system used in making the claimed cationic emulsions of hydrophobic benefit agents is preferably a cationic particulate material, comprising an inorganic moiety, or an organic moiety, or a hybrid of inorganic and organic moieties. This particulate component of the emulsifier system has a relatively high cationic surface charge (as determined by methods known in the art), as characterized by a zeta potential value of at least +25 millivolts, and a particle size of less than 2 microns, preferably much less than 1 micron. Unexpectedly, it has been found that one way to produce the cationic emulsifier particles that would serve the object of the present invention is by combining certain water-soluble cationic polymers with at least one water-insoluble anionic polymer, so long as certain material property, composition, and processing requirements are met during the manufacturing of the particles. These water-insoluble, polymeric particles bear a relatively high cationic surface charge which stabilizes them against particle-to-particle aggregation. Ordinarily, these particles do not form any particulate network structures, being stable against aggregation, and are typically much smaller than 1 micron in size.

Yet another important embodiment requires that, preferably, medium to very high molecular weight cationic polymers, more preferably, high molecular weight cationic polymers having a molecular weight in the range of 300,000-1,000,000 Dalton, and most preferably, certain combinations of high molecular weight and ultra high molecular weight (molecular weight>1,000,000 Dalton) cationic polymers are used as an emulsifier component to render the emulsion droplets cationic. Nonetheless, in order for a cationic particulate material or a cationic polymer to serve as an emulsifier, it is required to adsorb at the oil-water interface.

One way to achieve good interfacial adsorption of cationic polymers is to use cationic, amphiphilic copolymers that have both hydrophilic and hydrophobic segments in the polymer chain. Such copolymers could adsorb at the oil-water interface with their hydrophobic segments anchored onto the oil phase. Albeit, such copolymers might be functionally suitable for the present invention, they tend to be costly. The other type of cationic polymer that might be effective, are the hydrophobically-modified cationic polymers which also tend to be expensive.

Hydrophilic cationic polymers are relatively low-cost materials, and hence are preferred for the compositions and methods described herein. These polymers, however, may not be sufficiently surface-active for adsorption at the oil-water interface. Therefore, according to an important embodiment of the present invention, anionic polymers and surfactants that are capable of adsorbing at the oil-surface are used to facilitate the interfacial adsorption of the hydrophilic cationic polymers. These anionic polymers or surfactants electrostatically attract, onto themselves, the cationic polymers, serving as a coupling agent for the cationic polymers to co-adsorb at the interface. In effect, the emulsifier system is a combination of the hydrophilic cationic polymers and the surface-active anionic polymers or surfactants. Another embodiment of the compositions and methods described is to have the ratio of weights of the anionic and cationic components of the emulsifier system such that the emulsion droplets are cationic. Yet another embodiment is to use water-insoluble, hydrophobic, anionic polymers or surfactants as the anionic component of the emulsifier system.

As indicated above, the most preferred option for the cationic component of the emulsifier system is to use certain combinations of high molecular weight (molecular weight in the range of 50,000-1,000,000 Dalton) and ultra high molecular weight (molecular weight>1,000,000 Dalton) cationic polymers. Since a very high molecular weight polymer can flocculate emulsion droplets by what is known as bridging flocculation, for the object of the present invention, it is important that the cationic charge of the emulsion droplets is relatively high, for example, wherein the droplets show a cationic zeta potential of more than 25 millivolts, as measured using the methods known in the art. Bridging flocculation of suspended particles occurs when a single polymer chain simultaneously adsorbs on more than one particle. Accordingly, before undergoing bridging flocculation by a polymer chain, two or more suspended particles must approach one another as closely as where the particle-to-particle separation distance is equal to or less than the length of the polymer chain. Such close approach of the suspended particles may not be possible if there is sufficient electrostatic repulsion between the particles due to their surface charge, inhibiting the prospects of bridging flocculation even by a very high molecular weight polymer.

It was found during the research leading to the compositions and methods described herein that concentrated emulsions of hydrophobic benefit agents could be produced more easily, using the aforementioned emulsifier system, if, prior to emulsification, the oil phase was thickened using a specific type of a particulate-based thickener, with the thickener particles dispersed homogeneously in the oil phase. High-shear mixing was required to ensure good dispersion of the particulate thickener in the oil phase, in turn producing a viscous composite material comprising a hydrophobic liquid and the dispersed thickener particles. In order to serve the object of the present invention, it is highly desirable that the Hamaker constant, a direct proportionality factor for a measure of van der Waals attraction between material bodies, of the particulate-based thickener is such that the Hamaker constant (as may be derived using methods described in the colloid chemistry literature) of the composite oil phase is significantly higher, at least 4% higher, than that of a hydrophobic benefit agent by itself.

The most widely used particulate-based thickeners include the layered silicate materials such as the smectite clays, namely bentonite and hectorite clays, as well as fumed metal oxides, for example, silica. Layered silicate materials are a class of inorganic particulate materials that occur as stacks of individual, planar silicate layers referred to as platelets in the clay literature. These materials, as well as fumed silica, however, are hydrophilic in terms of surface property. Therefore, unless their surface is rendered hydrophobic, these materials can be used only as thickeners for water-based compositions but not for hydrophobic liquids. Various methods are known in the art for hydrophobic surface-modification of these materials, including treating the materials with long-chain (C8-C22) quaternary ammonium compounds, amphiphilic copolymers, and silanes.

In order to achieve the full advantage of the compositions and methods described herein, the specific type of particulate-based thickeners that are suitable include the hydrophobically-modified smectite clays for which only the face-surfaces of the clay platelets are rendered hydrophobic by the adsorption of long-chain (C8-C22) onium ions, e.g., from quaternary ammonium compounds, while the edge-surfaces remain hydrophilic and bears an anionic charge when wetted by an aqueous solution having a pH of greater than 3. Among the particulate-based thickeners, the materials that lend themselves easily to selective surface-modification are the smectite clays, because of the differences in the surface properties between the face surfaces and the edge surfaces of the clay platelets. The face-surfaces of smectite clays bear an anionic charge due to the isomorphic substitution of aluminum by magnesium in the clay-crystal structure. On the other hand, the electrical charge of the edge-surfaces depends on the type (anionic or cationic) of potential determining ions that adsorb on the edge surfaces when the clay platelets are dispersed in water or in an electrolyte solution. Under controlled solution (water-based) conditions, long-chain (C8-C22) quaternary surfactants can be made to adsorb only on the face-surfaces of clay platelets via ion-exchange, acting as counterions for the anionic platelet surface charge. The typical loading level for the quarternary ammonium compound can be in the range of about 10-80% by weight based on the dry weight of the smectite clay.

An important feature of one embodiment of the compositions and methods described herein relates to the final viscosity of the composite material (oil phase) containing the benefit agent, prior to the emulsification of the oil phase. The final (low shear-rate, e.g., 0.5-2 rpm of spindle speed in a Brookfield viscometer) viscosity of the composite is preferably greater than 5,000,000 cps, more preferably greater than 1,000,000 cps, and most preferably greater than 5,000,000 cps, with the viscosity measured using a Brookfield viscometer. The viscosity of the composite is preferably so high that the oil phase takes on a "stiff" consistency. In order to achieve this final viscosity, the hydrophobically-modified smectite clay thickener is adequately exfoliated or delaminated (separation of clay platelets across their face surfaces, as described in the art) in the oil phase, using high-shear dispersion methods known in the art.

In addition to one or more particulate-based thickeners, the oil phase may further contain other particulate materials in the form of inorganic and organic solids or liquids. In other words, the oil phase itself can be a dispersion of an inorganic or an organic solid, or an emulsion of an inorganic or an organic liquid, comprising two or more immiscible liquids.

Yet another embodiment of the compositions and methods described herein pertains to the hydrophobic or oil-based benefit agents that are appreciably soluble in concentrated solutions of detersive surfactants, typically used in various cleansing products. According to the compositions and methods described herein, such benefit agents are either dissolved, dispersed, or diluted in one or more hydrophobic solvent or liquid that has a relatively low solubility in concentrated surfactant solutions, in order to minimize the dissolution of the benefit agent in the detersive surfactant solutions. These hydrophobic solvents have a solubility of less than 2% by weight in an aqueous surfactant solution containing at least 3% (preferably 3%) by weight of one or more surfactant. The oil-phase, comprising one or more benefit agent and the hydrophobic solvent, is subsequently thickened using an organophilic smectite clay of the type noted above, followed by emulsification of the viscous, composite oil-phase using the aforementioned emulsifier system. The increased viscosity of the composite oil phase, due to the formation of a particulate network structure of the exfoliated organophilic clay, is expected to provide an addition barrier to the diffusion of the benefit agent from the oil phase to the surrounding aqueous phase of the emulsion or of the final cleansing product composition. The concentrated emulsions thus produced are eventually mixed or diluted with reagents selected from surfactants, polymers, and/or hydrophilic solvents to produce the compositions described herein.

According to one embodiment of the present invention, the claimed compositions are produced upon mixing or diluting the foregoing cationic O/W emulsions of the benefit agent with reagents selected from surfactants, hydrophilic solvents including water, glycols, alcohols, and glycerol, solid (e.g., smectite clays, waxes) or liquid particulate materials.

The resulting cationic emulsions of the benefit agents are highly stable against coalescence, the phenomenon that leads to the separation of the oil phase from the water phase in O/W emulsions. The stability (tested using methods known in the art) is retained even when the emulsions are diluted with water, for example, in the amount of 1 part by weight of emulsion to 50 parts by weight of water.

In the aforementioned emulsions, the individual cationic emulsifier particles remain adsorbed on the emulsion droplets in a manner such that these particles are able to function as an emulsifier. The total amount of cationic charge of the particles adsorbed on individual oil droplets is sufficiently high for offsetting any anionic charge due to any anionic component contained in the oil phase, such that the net surface-charge of the emulsion droplets is strongly cationic (characterized by a zeta potential of at least +25 millivolts). The surface properties, including hydrophobicity and surface charge (as defined and characterized by methods known in the art), of these cationic particles and the benefit agent composite are such that the cationic particles can remain adsorbed on the surface of the benefit agent composite. The enhanced substrate-deposition of the benefit agents from the claimed compositions, to a large extent, is attributed to having the cationic emulsifier particles pre-adsorbed on the emulsion droplets containing the benefit agent.

In addition, by emulsifying the benefit agents using an emulsifier system comprising pre-formed, discrete particles that are highly stable against coagulation, and hence remain adsorbed at the oil-water interface as individual or segregated particles, the benefit agent is not subjected to encapsulation within any capsule-like enclosure. This allows full manifestation of the intended benefits (for example, fragrance emission and hair conditioning), once the benefit agents deposit onto the substrates being treated by the compositions described herein. We now have also found that the foregoing cationic emulsions of the hydrophobic benefit agents do not adversely affect the foaming properties of surfactant-laden claimed compositions to any profound extent.

A distinguishing feature of the present invention over the prior art is that the emulsifier system used in producing the aforementioned additive-form for the benefit agent, is not a surfactant type of an emulsifier, but rather comprises at least two components: i) a cationic particle having a relatively high surface charge (at least +25 millivolts of, zeta-potential) and a particle size of less than 2 microns; and ii) a surface-modified smectite clay that is dispersible in a water-immiscible organic liquid but not in water, with the clay modified by the adsorption of onium ions, e.g., obtained by dissolution of C8-22 alkyl ammonium compounds onto specific sections of the clay surface. Also, in order for this emulsifier system to work, component (i) can be added only to the water phase and component (ii) only to the oil phase of the claimed O/W emulsions of benefit agents.

Another distinguishing feature is that the emulsified oil phase with a benefit agent contained therein, prior to emulsification, is a composite material providing for several beneficial features important to achieve certain objects of the present invention, such as: i) the composite material containing the benefit agent is considerably more viscous than the benefit agent itself, with the viscous consistency retained even upon heating; ii) the Hamaker constant of the composite material is considerably higher (at least 4% higher) than that of the benefit agent; and iii) the specific gravity of the composite material can be in the range of $\geq 1$.

A further distinguishing feature is that the benefit agent is not encapsulated in its entirety within a capsule wall, and accordingly there is no solid shell-wall separating an inner core comprising the benefit agent, from the surrounding solution phase of any cleansing or wash-off product composition that were to contain the benefit agent. Rather, the benefit agent composite is bonded to a particulate-based, cationic deposition-aid material that also serves as an emulsifier for the O/W emulsion of the composite material in water, without forming any capsule-like enclosure around the composite.

An additional distinguishing feature of one embodiment of the compositions and methods described herein is that a very high molecular weight polymer, with a weight average molecular weight exceeding 1,000,000 Dalton, often referred to in the prior art as deposition polymer, is an integral part of the multi-component emulsifier system used to emulsify the benefit agent-laden composite oil phase in a water phase, unlike in the prior art compositions wherein such a deposition polymer is not pre-adsorbed or bound to any non-encapsulated hydrophobic benefit agent emulsified in the water phase of these compositions.

DETAILED DESCRIPTION

The compositions described herein comprise the following ingredients:
  Reagents selected from the group consisting of surfactants and hydrophilic solvents and mixtures thereof, with the surfactants selected from the group consisting of anionic, nonionic, zwitterionic, and cationic surfactants, and the hydrophilic solvents selected from water, alcohols, glycols, and glycerine;
  Benefit agent selected from the group consisting of hydrophobic compounds, oils, oil-soluble or dispersible compounds, and water-immiscible compounds, offering hair-care, skin-care, fabric-care, and/or aesthetic or sensory property-boosting benefits.

Depending on the type of final products in which they are used as, i.e., shampoo, liquid soap, bodywash, laundry detergent, fabric softener, toothpaste, antiseptic ointments, these compositions may further contain ingredients selected from fatty alcohols having 8 to 22 carbon atoms, opacifiers or pearlescers such as ethylene glycol esters of fatty acids (e.g., ethylene glycol distearate), viscosity modifiers, buffering or pH adjusting chemicals, water-soluble polymers including cross-linked and non cross-linked polymers, foam boosters, perfumes, dyes, coloring agents or pigments, herb extracts, preservatives, hydrotopes, enzymes, bleaches, fabric conditioners, optical brighteners, antioxidants, stabilizers, dispersants, soil release agents, anti-wrinkle agents, chelants, anti corrosion agents, and teeth cleansing and whitening agents, and mixtures thereof.

In producing the claimed compositions, the benefit agents are incorporated into the compositions as cationic oil-in-water (O/W) emulsions of a viscous composite material containing the benefit agent(s). The cationic emulsion of the benefit agent(s) is produced using a multicomponent, particulate-based emulsifier system comprising mixtures of certain hydrophilic cationic polymers and water-insoluble or surface-active anionic polymers. In effect, the benefit agent(s) is contained in these emulsions as part of a viscous, emulsified oil-phase, with the emulsion droplets bonded to interfacially-active, cationic particles serving as emulsifier, comprising the aforementioned polymers. By interfacially-active is meant the ability to adsorb at an interface, for example, oil-water and air-water interfaces.

The benefit agents that have appreciable solubility in concentrated (amount $\geq 3\%$ by weight) surfactant solutions, are first dissolved or dispersed or diluted in a suitable hydrophobic cosmetically acceptable liquid or solvent that has a relatively low ($<1\%$ by wt.) solubility in concentrated surfactant solutions. A particularly useful cosmetic-solvent is a triglyceride, while equally useful is a silicone fluid, preferably a dimethicone fluid.

Preceding emulsification, the oil-phase, comprising a hydrophobic, water-immiscible liquid or solvent with the benefit agent(s) contained therein, is thickened using one or more organophilic smectite clay for which only the face-surface of the clay platelets is rendered hydrophobic, while the edge-surface remains hydrophilic, while capable of bearing an anionic surface charge when exposed to aqueous solutions at a pH of $\geq 3$. Upon thickening, the oil phase preferably has a viscosity of greater than 5,000,000 cps, as measured using a Brookfield RVT viscometer operated at 1 rpm (revolution per minute) of spindle speed with spindle number 7.

The various aspects of the aforementioned compositions are discussed in greater detail below:

Surfactants

Non-limiting examples of suitable anionic surfactants are the sodium, ammonium, and mono-, di-, and tri-ethanolamine salts of alkyl sulfates, alkyl ether sulfates, alkaryl sulfonates, alkyl succinates, alkyl sulfosuccinate, N-alkoyl sarcosinates, alkyl phosphates, alkyl ether phosphates, alkyl ether carboxylates, and α-olefin sulfonates. The alkyl groups generally contain from 8 to 18 carbon atoms and may be unsaturated. The alkyl ether sulfates, alkyl ether phosphates, and alkyl ether carboxylates may contain from 1 to 10 ethylene oxide or propylene oxide units per molecule, and preferably contain 2 to 3 ethylene oxide units per molecule. Examples of the most preferred anionic surfactants include sodium or ammonium lauryl sulfate and sodium or ammonium lauryl ether sulfate.

Suitable nonionic surfactants include, but not limited to, aliphatic, primary or secondary linear or branched chain alcohols or phenols with alkylene oxides, generally ethylene oxide and generally 6-30 ethylene oxide groups. Other suitable nonionic surfactants include mono- or di-alkyl alkanolamides, alkyl polyglucosides, and polyhydroxy fatty acid amides.

The amphoteric surfactants suitable for use in the present invention include alkyl amine oxides, alkyl betaines, alkyl amidopropyl betaines, alkyl sulfobetaines, alkyl glycinates, alkyl carboxyglycinates, alkyl amphopropionates, alkyl amidopropyl hydroxysultaines, acyl taurates, and acyl glutamates wherein the alkyl and acyl groups have from 8 to 18 carbon atoms.

Nonlimiting examples of suitable cationic surfactants include water-soluble or water-dispersible or water-insoluble compounds containing at least one amine group which is preferably a quaternary amine group, and at least one hydrocarbon group which is preferably a long-chain hydrocarbon group. The hydrocarbon group may be hydroxylated and/or alkoxylated and may comprise ester- and/or amido- and/or aromatic-groups. The hydrocarbon group may be fully saturated or unsaturated.

The level of surfactants may range from 0.5 to 95%, preferably from 2 to 90%, and most preferably from 3 to 90% by weight of the claimed compositions.

Hydrophilic Solvents

The hydrophilic solvents suitable for use include water and hydrophilic organic liquids and mixtures thereof. Nonlimiting examples of preferred hydrophilic organic liquids include glycerol, ethanol, isopropanol, propylene glycol, butylene glycol, hexylene glycol, polyethylene glycol and mixtures thereof.

The level of hydrophilic solvents may range from 0.1 to 95%, preferably from 1 to 90%, and most preferably from 3 to 90% by weight of the claimed compositions.

Benefit Agents

In the compositions and methods described herein, benefit agents are water-insoluble but oil-soluble/miscible/dispersible solids and liquids, as well as oily materials, that can provide a positive or beneficial effect to the substrate being treated, e.g., to the hair, skin, fabric, and teeth. Preferred benefit agents include, but not limited to, the following:
 a) silicone oils, resins, and modifications thereof such as linear and cyclic polydimethylsiloxanes, amino-modified, alkyl, aryl, and alkylaryl silicone oils, which preferably have a viscosity>>50,000 cst;
 b) fragrance, perfumery, and essential oils and resins;
 c) organic sunscreen actives, for example, octylmethoxy cinnamate;
 d) antimicrobial agents, for example, 2-hydroxy-4,2,4-trichlorodiphenylether;
 e) ester solvents; for example, isopropyl myristate;
 f) lipids and lipid like substance, for example, cholesterol;
 g) hydrocarbons such as paraffins, petrolatum, and mineral oil
 h) fish and vegetable oils
 i) hydrophobic plant extracts;
 j) therapeutic and skin-care reagents;
 k) hydroquinone
 l) waxes; and
 m) pigments including inorganic compounds with hydrophobically modified surface and/or dispersed in an oil or a hydrophobic liquid.

One or more of the foregoing benefit agents is included in the compositions described herein in an amount varying from 0.05 to 99%, preferably from 0.1 to 40%, and most preferably from 0.5 to 20% by weight of the detersive composition. The benefit agents are incorporated into the detersive compositions by mixing or diluting concentrated emulsions of the benefit agents with detersive surfactants, wherein in the preferred embodiment, the emulsions are produced in accordance with the following sequential steps (i) through (iii).

i) Unless the benefit agent is insoluble or only sparingly soluble in surfactant solutions, for example, as with most silicones, the benefit agent is dissolved or dispersed or diluted in a hydrophobic liquid or solvent with poor surfactant-phase solubility (herein defined as having a solubility <2% by weight in an aqueous detersive surfactant solution with a surfactant content in the range of 3-25%). A preferred diluent is a triglyceride, castor oil, or a silicone fluid, dimethicone fluid, having a viscosity of >50 centistokes. The triglyceride- or dimethicone-content of the resulting oil-phase is preferably at least 50% by weight, e.g., 50-95% by weight, while the amount of the benefit agent is the range of 0.1-60%.

ii) The oil-phase containing the benefit agent, or the silicone-based benefit agent, is thickened using an organophilic smectite clay. Not all commercially available organophilic smectite clays are ideal for obtaining the full advantage of the compositions and methods described herein. The preferred organophilic smectite clays are those for which only the face surface is rendered hydrophobic by the adsorption of fatty quaternary ammonium compounds with 8 to 22 carbon atoms in the alkyl chain, while the edge-surface remains hydrophilic. Examples of suitable organoclays include, but not limited to, the organophilic bentonite clays available from Nanocor, a subsidiary of AMCOL International Corporation. The amount of organoclay added to the oil- or silicone-phase can be 3-60% by weight, preferably 20-50%, and ideally 25-45%, based on the weight of the oil- or silicone phase. In order to enhance the thickening ability of the organoclay, one or more polar materials such as propylene carbonate, ethanol, alkylene glycol, and water and mixtures thereof may be added at the level of 10-60% by weight, based on the weight of the organoclay. In producing the thickened oil- or silicone-phase, the organoclay is dispersed in the hydrophobic liquid using high-shear equipment such as rotor-stator homogenizer and extruder.

iii) The thickened oil- or silicone-phase is emulsified in water using an emulsifier system comprising in part a cationic particle having a relatively high cationic surface charge and a size of <2 microns. According to a preferred embodiment, the cationic particle component of the emulsifier comprises three polymeric components, an anionic polymer and two hydrophilic cationic polymers, as described in more detail to follow. However, not all three of these polymeric components of the emulsifier system are added to the emulsion batch at the same time. Two of the three components, the anionic polymer, and one of the cationic polymers are added to the batch prior to adding the third component. These two components are collectively referred to herein as part A of the emulsifier system. The third polymeric component, added at a later stage of the emulsfication process, is referred to herein as part B of the emulsifier system. As the first step of the emulsification process, the water-phase of the emulsion is prepared by combining in a given sequential fashion de-ionized water, the anionic polymer of part A of the emulsifier system, and a preservative, and subsequently homogenizing the mixture in a rotor-stator homogenizer, for example. The next step is to add the cationic polymer of part A of the emulsifier system, and subsequently homogenizing the mixture under high shear. The subsequent step is to add the thickened oil- or silicone-phase to the water-phase, while the batch remains under agitation. Subsequently, the batch is homogenized using high-shear agitation provided by an agitator. Once the emulsion has formed and the composition looks uniform, part B of the emulsifier system is added, and the emulsion is homogenized further.

In addition to the aforementioned ingredients, the emulsion may further contain ingredients such as one or more pH adjustment chemicals, buffering chemicals, one or more water-phase thickener selected from non-ionic and cationic polymer-based thickeners, and one or more optical brightener pigments. The amount of thickened oil- or silicone-phase in the emulsion may range from 10 to 60% by weight of the final composition, but most preferably from 25 to 45%.

The concentrated emulsions of the benefit agents thus produced are mixed or diluted with one or more detersive surfactants present either in aqueous solutions or in powder/granular forms, in producing the detersive compositions of the present invention. The concentrated emulsions are incorporated into surfactant-containing aqueous compositions at levels varying from 1 to 60% by weight of the final compositions. These emulsions are required to be such that the surface charge of the emulsion droplets is strongly cationic (as may be determined by measuring the zeta-potential of the emulsion droplets using a method known in the art), prior to mixing the emulsions with the detersive surfactants. In order to achieve the relatively high cationic charge of the emulsion droplets, the ratio of the weight of the anionic component to the weight of the cationic components of the emulsifier system may vary from 1:0.5 to 1:30, more preferably from 1:1 to 1:20, and most preferably from 1:2 to 1:10, respectively. The ratio of the weight of the cationic polymer comprising part A of the emulsifier system to the weight of the cationic polymer comprising part B of the emulsifier system is in the range of 1:0.01-1:10, more preferably in the range of 1:0.05-1:5, and most preferably in the range of 1:0.1-1:1.

Emulsifier System

As noted above, in accordance with the compositions and methods described herein, the emulsifier system used in producing the concentrated, cationic emulsions of the benefit agents is comprised of three essential components: (1) an anionic polymer that is sufficiently surface-active for adsorption at the oil-water interface, and is preferably water-insoluble; (2) a medium-to-high molecular weight, hydrophilic, cationic polymer that is virtually insoluble (soluble less than 1.0% by weight) in 3 weight % or higher anionic surfactant solutions; and (3) a high-to-very high molecular weight, hydrophilic, cationic polymer. In mixing components (1) and (2) to produce part A of the emulsifier system, the anionic polymer is dissolved or dispersed in water, prior to adding the cationic polymer (component 2). For the anionic polymers having weak-acid groups, for example, the phosphate and carboxylate groups, a base is added prior to adding component (2), in order to ensure that these anionic groups are fully or partially dissociated, producing anionic charge sites on the polymer chain. Component (3) is preferably added at a later stage of emulsification. Although components (2) and (3) are both hydrophilic, cationic polymers, they are preferably not interchangeable in terms of their order of addition, in order to achieve the full advantage of the compositions and methods described herein.

We have now found that Part A of the emulsifier system essentially comprises a colloidally-stable particulate material having a relatively high cationic surface charge (as inferred from the zeta-potential of the dispersed particles, measured using a method known in the art), and colloidal (i.e., less than 2 micrometer) particle size (as measured, based on video microscopy, and using a Malvern Zetasizer, Nano-ZS, particle size analyzer). By colloidal-stability is meant stability against particle aggregation or flocculation, which may be determined using methods (e.g., determining particle size as a function of time, stability under large centrifugal forces, measuring dispersion viscosity as a function of shear-rate) known in the art.

Component (1)

This is selected from water-soluble anionic polymers, such as polyphosphate, polysulfonates (e.g., polyvinyl sulfonate, lignosulfonates), polycarboxylates (e.g. sodium polyacrylate), polysulfates (e.g., polyvinyl sulfate), and silicone polymers with a pendant anionic group selected from carboxylate, sulfate, and phosphate groups. The polymer is sufficiently surface-active for adsorption at the oil-water interface, if it is capable of reducing the surface tension of water, when added at a level of 1% by weight, preferably reducing the surface tension by at least 15%.

A preferred anionic polymer is a water-insoluble but oil-soluble, liquid copolymer of castor oil phosphate and 3-isocyanatomethyl-3,5,5-trimethyl cyclohexyl isocyanate, referred to herein as castor oil phosphate/IPDI copolymer. This liquid copolymer is preferred because of its relatively low solubility (2 weight % or lower in surfactant solutions containing 3 weight % or higher amount of surfactant) in surfactant solutions, and because the liquid form is expected to yield less rigid (i.e., softer) cationic particles used as the emulsifier in accordance with the present invention.

Component (2)

This is selected from hydrophilic, cationic polymers with a relatively high cationic charge content of least 6% by weight of cationic nitrogen group, and having a preferred molecular weight in the range of 50,000-600,000 Dalton, more preferably in the range of 200,000-500,000 Dalton, and most preferably in the range of 300,000-500,000 Dalton. According to an important embodiment, the polymer should be insoluble in concentrated solutions (amount at least 3% by weight) of anionic surfactants. Insolubility is defined as soluble less than 1.0%, preferably less than 0.5% by weight, in a 3% by weight or greater aqueous anionic surfactant solution. The most suitable polymer is poly(diallyl dimethyl ammonium chloride) which will be referred to herein as Poly(DADMAC). It has a cationic nitrogen content of about 8.67% by weight. Due to their relatively high solubility in concentrated surfactant solutions, examples of hydrophilic cationic polymers which may not be best suited to serve as component (2) of the aforementioned emulsifier system include copolymers of DADMAC and acrylamide monomers, also known as polyquaternium-7, quaternized copolymers of vinylpyrrolidone and dimethylaminomethylmethacryalte, also known as polyquaternium-11, copolymer of vinylpyrrolidone and methacrylamidopropyltrimethylammonium chloride, also known as polyquaternium 28, and cationic derivatives of natural polymers such as cellulose, starch, and guar gum. Some of these polymers, however, may be suitable as component (3) of the emulsifier system.

Component (3)

This is selected from high-to-very high molecular cationic polymers having molecular weight preferably in the range of greater than 600,000 Dalton, more preferably in the range of 2,000,000-6,000,000 Dalton, and most preferably in the range of 1,000,000-4,000,000 Dalton. The cationic charge content of these polymers is preferably in the range of 0.1-4.5% by weight of cationic nitrogen group. Examples of such polymers include cationic copolymers of acrylamide, and cationic derivatives of natural polymers such as cellulose ether polymers, guar gum, and starch. The most preferred component (3)-polymer are the cationic derivatives of cellulose, guar, and starch.

The following examples will more fully illustrate the preferred embodiments within the scope of the present invention. These examples are solely for the purpose of illustration and are not to be construed as limitations of the present invention as many variations thereof are possible without departing from the purview and spirit of the compositions and methods described herein.

EXAMPLE I

This example shows the thickened compositions of some benefit agents that could be used in producing the detersive compositions of the present invention. In producing the thickened fragrance composition (shown in Table I), the fragrance material(s) was first mixed with a triglyceride, castor oil. The organoclay was added to this mixture in small portions, while the batch remained under mixing in a rotor-stator homogenizer (Silverson). Once the entire amount of the organoclay was added, the homogenizer speed was gradually increased to about 8,000-10,000 rpm, and the batch was homogenized until lump-free and viscous. The silicone- and castorlatum-based benefit agents were thickened following a procedure similar to the one above, except that these benefit agents were not diluted in a triglyceride prior to undergoing thickening. Also, once the composition appeared to be lump-free, a polar activator, propylene carbonate, was added, and the batch was subsequently homogenized further until it looked uniform and viscous. The organophilic smectite clay used in Mix Nos. 1, 3, and 5 is an organophilic sodium bentonite clay from AMCOL International Corporation, while a mixture of two different organophilic sodium bentonite clays was used in Mix No. 4.

TABLE I

| | Weight % | | | | |
|---|---|---|---|---|---|
| Ingredient | Mix 1 Benefit Agent: Fragrance | Mix 2 Benefit Agent: Castorlatum | Mix 3 Benefit Agent: Silicone | Mix 4 Benefit Agent: Silicone | Mix 5 Benefit Agent: Silicone |
| Triglyceride: Castor Oil | 48.13 | | | | |
| Fragrance | 24.07 | | | | |
| Castorlatum 1 | | 72.71 | | | |
| Dimethicone Fluid, 60,000 cst | | | 29.35 | | 11.58 |
| Dimethicone Fluid, 10,000 cst | | | 15.05 | 15.19 | |
| Dimethicone, 5,000 cst | | | 22.17 | | |
| Dimethicone, 350 cst | | | | 46.24 | 38.61 |
| Dimethicone, Gum 2 | | | | 20.48 | 19.31 |
| Phenyl Trimethicone | | | | | 7.72 |
| Bentonite Clay 3 | | 15.78 | | | |
| Organophilic Bentonite Clay 4 | 27.8 | | 25.67 | 14.38 | 18.53 |
| Fatty Quaternary Ammonium Compound 5 | | 8.61 (6.46 - active) | | | |
| Propylene Carbonate | | 2.9 | 7.76 | 3.71 | 4.25 |

1: A proprietary blend of castor oil and hydrogenated castor oil from CasChem
2: SF 76 from General Electric Silicones
3: Sodium Bentonite clay from AMCOL International Corporation
4: Organo-34 from AMCOL, Bentone 34 from Elementis
5: Q₂C from Tomah products, 75% active

EXAMPLE II

This example presents the typical composition and manufacturing procedure for the cationic emulsions of benefit agents, produced in accordance with the present invention. The cationic polymer for the part A of the emulsifier system is poly(DADMAC), Zetag 7122 (20% active), received from Ciba Specialty Chemicals. The anionic polymer for the part A of the emulsifier system is castor oil phosphate/IPDI copolymer, Polyphos PPI-CO, received from Alzo International Inc. The cationic polymer for the part B of the emulsifier system is cationic hydroxyethyl cellulose, Ucare Polymer JR 30M, received from Amerchol Corporation.

In producing the part A of the emulsifier system, the anionic polymer (water-insoluble) was dispersed (resulting in a pale white-colored dispersion) in de-ionized water after adding a 50% solution of sodium hydroxide to the water, using a rotor-stator homogenizer (Silverson). Zetag 7122 was added next, slowly, while the batch was being homogenized at a speed of about 5,000-7,000 rpm. Once the addition of Zetag 7122 was complete, the batch was homogenized at a speed of 7,000-8,000 rpm, while maintaining ambient temperature (20-250 C) for the batch by applying cooling. Typically, when the batch comprised a total weight of about 1.5-2 kg, based on the above ingredients, it was homogenized for a period of about 10 minutes. During the course of this homogenization process, the dispersion batch exhibited a milky white appearance. Subsequently, a small amount of a preservative, phenonip, received from Clariant, was added to the batch, following which the batch was homogenized for an additional 10 minutes. The resulting dispersion would typically exhibit the following characteristics in terms of particle size: i) when diluted by about 2.8× with water, the dilute dispersion would filter through a Whatman grade No. 40 filter paper under an applied suction, leaving virtually no solid residue on the filter paper; ii) the particle size, as measured based on video-microscopy or on a Malvern Zetasizer particle size analyzer would indicate that the particle size is in the colloidal range, i.e., less than 2 micron; and iii) the particles are sufficiently small for to be able to resist centrifugal separation (i.e., virtually no separation of the dispersed material) when the dispersion (having a Brookfield viscosity of <200 cps for the spindle-speed range of 1-10 rpm) is centrifuged at 4,500 rpm for a period of 30 minutes.

Once the part A of the emulsifier system was produced as described above, the thickened benefit agent composite-phase was added to the batch in small portions, while keeping the batch under high-speed agitation using a dispersion blade agitator. The mixture was homogenized adequately under high-shear agitation to form a homogeneous emulsion. Polymer JR 30M was added next in the form of an aqueous solution containing 2% by weight of the polymer. The emulsion was homogenized further, following the addition of the polymer solution. The composition for the resulting final emulsion is presented in Table II, wherein the Brookfield viscosity of the final emulsion is at least 10,000 cps at 1 rpm of spindle speed.

TABLE II

| Phase | Ingredient | Weight % (within ± 0.01%) |
|---|---|---|
| Part A of the Emulsifier System | | |
| Water | Deionized water | 18.43 |
| | 50% Sodium Hydroxide | 0.12 |
| | Castrol Oil Phosphate/IPDI Copolymer | 0.69 |
| | Zetag 7122 (20 wt. % active) | 17.00 (3.4 active) |
| | Phenonip | 0.41 |
| Thickened Benefit Agent | | |
| Oil | Thickened Benefit Agent Part B of the Emulsifier System | 39.10 |
| Water | 2% Polymer JR-30M Solution (2 wt. % active) | 24.25 (0.49 active) |

EXAMPLE III

This example describes the composition, manufacturing procedure, and performance properties of the detersive compositions produced in accordance with the preferred embodiments.

Composition

Conditioning (i.e., 2-in-1 type) shampoos, Shampoo Nos. 1 and 2, were manufactured using a dimethicone (silicone) emulsion prepared as per the specifications in EXAMPLE II, wherein the thickened silicone composition corresponds to Mix No. 5 in Table I of EXAMPLE I. The thickened silicone compositions used in producing the dimethicone emulsions contained in Shampoo No. 3 and in Bodywash No. 1, as per the specifications in EXAMPLE II, correspond to Mix Nos. 4 and 3, respectively, in Table I. Bodywash No. 2 contained a castorlatum emulsion produced as per the specifications in EXAMPLE II, using the thickened castorlatum composition of Mix No. 2 in Table I.

TABLE III

| Phase | Ingredients | Shampoo 1 | Shampoo 2 | Shampoo 3 | Bodywash 1 | Bodywash 2 |
|---|---|---|---|---|---|---|
| A | Deionized Water | 23.150 | 20.650 | 24.480 | 1.575 | 11.480 |
| A | Hydroxyethyl Cellulose 1 Solution | 10.000 (2% active) | 10.000 (2% active) | 8.92 (2.5% active) | 2.000 (1% active) | 4.400 (2.5% active) |
| B | Ammonium Laureth-3 Sulfate (28% active) | 35.725 | 35.725 | 35.725 | | 33.750 |
| B | Ammonium Lauryl Sulfate (28% active) | 21.425 | 21.425 | 21.425 | | 11.250 |
| B | Cocamidopropyl Betaine (31% active) | | | | | 17.420 |
| B | Ammonium Laureth-2 Sulfate (25.5% active) | | | | 47.100 | |
| B | Disodium Laureth Sulfosuccinate (32% active) | | | | 21.875 | |
| C | Cocamide MEA (92% active) | 1.000 | 1.000 | 1.000 | 3.000 | |
| C | Ethylene Glycol Distearate | 1.500 | 1.500 | 1.500 | 1.500 | 1.500 |
| C | Ammonium Chloride | 1.000 | 1.000 | 1.000 | | 1.000 |
| C | Sodium Chloride | | | | 1.000 | |
| D | Preservative 2 | 0.200 | 0.200 | 0.200 | 0.200 | 0.200 |
| D | Color Solution | 0.500 | 0.500 | 1.500 | 1.500 | 0.500 |

TABLE III-continued

| Phase | Ingredients | Shampoo 1 | Shampoo 2 | Shampoo 3 | Bodywash 1 | Bodywash 2 |
|---|---|---|---|---|---|---|
| D | Fragrance | 0.500 | 0.500 | 0.500 | 1.000 | 0.500 |
| E | Benefit Agent Emulsion | 5.000 (1.5% Dimethicone) | 2.500 (0.75% Dimethicone) | 3.750 (1.2% Dimethicone) | 19.250 (5% Dimethicone) | 18.000 (5.15% Castorlatum) |

1: Cellosize Polymer PCG-10 from Amerchol Corporation
2: DMDM Hydantoin (Tradename: Glydant) from Lonza Manufacturing Procedure Combine the Phase A ingredients under gentle agitation.

Add the Phase B ingredients to the batch and start heating the batch to about 75-85° C., while the batch remains under gentle agitation.

Once the temperature reaches about 60° C., add the Phase C ingredients under continued gentle agitation.

Start cooling the batch, once the solids dissolve and the batch looks uniform.

Upon cooling the batch to about 30-35° C., add the phase D ingredients.

Add phase E and continue mixing until homogeneous.

Performance Evaluation

Shampoo

A primary function or benefit of a hair-conditioning agent is to reduce the hair-combining strength, especially when the hair is wet. The silicone deposition efficiency of the shampoo compositions of the present invention was evaluated by conducting panel testing. Shampoo No. 1 of Table III was tested against a reference product comprising a leading commercial conditioner product that is rated by the manufacturer to yield a good hair-conditioning level of 5 on a scale of 1 to 10 (the higher the number, the greater the level of conditioning). The panel testing was carried out at Cantor Research Laboratories, New York, wherein a panel of ten panelists was convened at two different times, i.e., a total of twenty panelists were involved in evaluating Shampoo No. 1. The test protocol followed is as follows. A technical staff from Cantor Laboratories washed the panelist's hair first with a clarifying shampoo free of silicone and any other hair-conditioning agent, in order to wash off any residual hair-conditioning agent from prior use. This washing process was repeated (typically 2-3 times) until the panelist and the technician individually rated the ease of combing for the wet hair at the score of 2-3 on a scale of 1-10 (the higher the number, the greater the ease of combing). The washed hair was dried and the dried hair was tested again for ease of combing individually by the panelist and the technician, following the same scoring protocol as noted above. Subsequently, the panelist's hair was split into two halves. Shampoo No. 1 was applied on one half, and the leading conditioner on the other half of the hair. Following complete rinsing of the two treated halves of the hair with water, the panelist and the technician evaluated the ease of combing of the wet hair using the above scoring protocol. This evaluation was repeated after the hair was dried. The panelist and the technician also rated the smoothness and the shine for the two halves of the dried hair. The composite average (averaged over all panelist scores and technician scores for all panelists) rating provided by the twenty panelists and the technician is presented in Table IV, wherein the term "enhancement" denotes the difference in score for a conditioning property between post-clarifying shampoo and post-shampoo 1 or post -conditioner (i.e., Score after shampoo No. 1 treatment or the conditioner treatment—Score after clarifying shampoo treatment), wherein a positive value for the "enhancement" score signifies an improvement in the hair-conditioning property; the higher the "enhancement" value, the greater the improvement). Following the panel testing method described above, the leading conditioner was tested (involving the same twenty panelists) also against a leading commercial conditioning (2-in-1 type) shampoo that is rated by the manufacturer to yield deep conditioning. Based on certain findings, this 2-in-1 shampoo appears to resemble shampoo No. 1 considerably, in terms of levels of detersive surfactants and the conditioning agents. The leading 2-in-1 shampoo contains a cationic deposition polymer, cationic hydroxyethyl cellulose. The average ratings for the two products are also presented in Table IV (Test 2).

TABLE IV

| Enhancement of Conditioning Property | Shampoo 1 (2-in-1 type) (Test 1) | Leading Conditioner (Test 1) | Leading 2-in-1 Shampoo (Test 2) | Leading Conditioner (Test 2) |
|---|---|---|---|---|
| Wet Combing | 3.25 | 3.15 | 1.38 | 3.5 |
| Dry Combing | 2.93 | 4.25 | 2.18 | 4.05 |
| Smoothness | 3.08 | 3.98 | 2.3 | 3.73 |
| Shine | 1.88 | 1.98 | 1.63 | 2.18 |

As evident from Table IV, the conditioning shampoo, Shampoo No. 1, an example of one embodiment of the present invention, came considerably close to matching the hair conditioning performance of a leading conditioner. In contrast, the leading commercial conditioning shampoo fell much short of the leading conditioner in providing for hair-conditioning. Based on similar panel testing as described above, it was also found that Shampoo No. 2 in Table III provided slightly better hair-conditioning, as compared to the leading commercial 2-in-1 shampoo (containing 1.2 wt. % dimethicone plus two additional conditioning oils), even though Shampoo No. 2 had a significantly lower level (0.75 wt. % dimethicone) of conditioning agent(s). Furthermore, the conditioning shampoo compositions described herein showed good foaming properties, no worse than the leading commercial conditioning shampoo. The test method used for evaluating the foaming property involves 20× dilution of the shampoo with water in a 100-mL graduated centrifuge tube, under mixing in a rotary mixer for 5 minutes, followed by noting the volume of the resulting foam in the centrifuge tube.

Bodywash

Skin moisturization, resulting from silicone deposition on the skin from Bodywash No. 1 in Table III, was evaluated by measuring the trans epidermal water loss (TEWL) before and after treatment of the skin with the bodywash, using a method known in the art. The panel testing (with six panelists) involving TEWL measurements, was carried out at Cantor Research Laboratories, New York. In order to put the results into a perspective, a leading commercial bodywash that contains cationic hydroxyethyl cellulose, presumably as a cationic deposition polymer, was tested alongside with Bodywash No. 1. The leading commercial bodywash product likely has a much higher (potentially as much as about 3×) level of a skin-moisturizing emollient, petrolatum, as compared to Bodywash No. 1, containing silicone as the skin-moisturizing agent. The reduction in the TEWL rate (a sign of skin moisturization) was about 2.7 unit with the leading commercial bodywash, closely followed by the 2.1 unit reduction in the TEWL rate with Bodywash No. 1.

In addition, the detersive compositions described herein have been evaluated for applications such as fabric softening and antiwrinkle (due to silicone deposition) and fragrance extension from laundry detergent wash, yielding results that further confirm the prospects of achieving good deposition of hydrophobic benefit agents from a wide variety of detersive compositions.

What is claimed is:

1. A composition comprising a mixture of water, a surfactant, and a hydrophobic benefit agent composite material in a particulate form having a mean particle size in the range of 1-1,000 micron, and a specific gravity of $\leq 1$, not encapsulated within a film or a capsule-like enclosure, wherein said hydrophobic benefit agent composite material comprises oil phase droplets of an oil-in-water emulsion formed by emulsifying water, at least one hydrophobic liquid, and a hydrophobically-modified smectite clay thickening agent with a deposition aid material comprising a surface-active or water-insoluble anionic polymer and a high molecular weight hydrophilic cationic polymer that is insoluble in 3 wt % or higher anionic surfactant solutions to form a thickened oil-in-water emulsion; and thereafter homogenizing the thickened oil-in-water emulsion with a hydrophilic, ultra high molecular weight cationic polymer to adsorb deposition aid material on the surface of the benefit agent composite droplets, wherein the adsorption of deposition aid material on the surface of the benefit agent composite droplets is achieved prior to the addition of ii) to i).

2. The composition of claim 1;

wherein the smectite is clay selected from the group consisting of natural and synthetic bentonite, hectorite, and mixtures thereof;

wherein the hydrophobic benefit agent has a viscosity of at least 500,000 cps, as measured using a Brookfield viscometer at 1 rpm of spindle speed, and a specific gravity of $\geq 1$; and wherein the hydrophobically-modified smectite clay comprises an onium ion compound is in an amount in the range of 10-70% by weight of the smectite clay and hydrophobic-modification by adsorption of the onium ion having a carbon atom chain length in the range of C8-C22 only the basal (face) surface of the smectite clay.

3. The composition of claim 1 wherein the deposition-aid material has a mean particle size in the range of 0.015-100 microns and comprises the anionic polymer and cationic polymer electrostatically coupled, the cationic polymer having a cationic charge content of at least 6% by weight of cationic nitrogen group and a molecular weight in the range of 50,000-600,000 Dalton.

4. The composition of claim 3 wherein the deposition-aid material has a zeta potential value of $\geq +25$ mV for the dispersed particlesas measured as in an aqueous solution at a pH in the range of 3-9.

5. The composition of claim 4, wherein the deposition-aid material has a mean particle size in the range of 0.015-10 microns.

6. The composition of claim 5, wherein the deposition-aid material has a mean particle size in the range of 0.015-1 micron.

7. The composition of claim 1 wherein the deposition-aid material is bound to a surface of the hydrophobically-modified smectite clay.

8. The composition of claim 1 wherein the composition comprises 10% to 60% by weight of the hydrophobic benefit agent composite.

9. The composition of claim 1 wherein the composition comprises 10% to 60% by weight of the hydrophobic benefit agent composite.

10. The composition of claim 3 wherein the anionic polymer is selected from the group consisting of water-insoluble anionic polymers with anionic groups selected from phosphate, carboxylate, sulfonate, and sulfate, and water-soluble, surface-active, anionic polymers selected from polysulfonates, polycarboxylates, polysulfates, and silicone polymers with pendant anionic groups selected from carboxylate, phosphate, and sulfate groups, that are capable of adsorbing at air-water interface or oil-water interface.

11. The composition of claim 10 wherein the water-insoluble, anionic polymer is a copolymer of castor oil phosphate and 3-isocyanatomethyl-3,5,5-trimethyl cyclohexyl isocyanate.

12. The composition of claim 3 wherein the cationic polymer is poly(diallyldimethyl ammonium chloride).

13. The composition of claim 3 wherein the deposition-aid material further comprises an ultra-high molecular eight cationic polymer, the ultra-high molecular weight cationic polymer having a molecular weight in the range of 600,000-10,000,000 Dalton, and a cationic charge content of at least 0.1-4.5% by weight of cationic nitrogen group.

14. The composition of claim 13 wherein the ultra-high molecular weight cationic polymer is selected from the group consisting of a cationic derivative of cellulose, a cationic derivative of guar, and a cationic derivative of starch polymers, and mixtures thereof.

15. The composition of claim 13 wherein the hydrophobic benefit agent was made by adding the high molecular weight cationic polymer to the anionic polymer and mixing or homogenizing the two components to form an admixture, then adding the admixture to at least one hydrophobic liquid and the hydrophobically-modified smectite clay and homogenizing the resulting mixture to form an emulsion, and then adding the ultra-high molecular weight cationic polymer and homogenizing the emulsion further.

16. The composition of claim 13 wherein the deposition-aid material comprises the anionic polymer component in the range of 0.1-5% by weight, based on the weight of the deposition-aid material.

17. The composition of claim 13 wherein the total amount of the two cationic polymer components of the deposition-aid material is from 0.5 to 30 times the weight of the anionic polymer, with the weight of the high molecular weight cationic polymer being from 0.01 to 10 times the weight of the ultra-high molecular weight cationic polymer.

18. The composition of claim 1 comprising 0.5-95% by weight of the surfactant.

19. The composition of claim 1 wherein the hydrophobic benefit agent comprises a material selected from the group consisting of silicone, fragrance, emollient, antimicrobial agent, sunscreen, lipid, oil, hydrocarbon, wax, hydrophobically-modified pigment, inorganic compound, and mixtures thereof.

20. The composition of claim 1 comprising 0.05% to 99% by weight of the hydrophobic benefit agent.

21. A method of depositing a hydrophobic benefit agent on a substrate comprising contacting the substrate with the composition of claim 1.

22. A method comprising contacting the composition of claim 1 with a substrate selected from the group consisting of hair, skin, and fabric.

* * * * *